US00PP24314P2

(12) United States Plant Patent
Zary

(10) Patent No.: US PP24,314 P2
(45) Date of Patent: Mar. 18, 2014

(54) SHRUB ROSE PLANT NAMED 'ZARSBJOH'

(50) Latin Name: *Rosa×hybrida*
Varietal Denomination: ZARSBJOH

(76) Inventor: Keith Zary, Troy, OH (US)

( * ) Notice: Subject to any disclaimer, the term of this patent is extended or adjusted under 35 U.S.C. 154(b) by 95 days.

(21) Appl. No.: 13/506,868

(22) Filed: May 22, 2012

(51) Int. Cl.
*A01H 5/00* (2006.01)

(52) U.S. Cl.
USPC ..... Plt./108; Plt./101; Plt./102

(58) Field of Classification Search
USPC ..... Plt./101, 102, 108
See application file for complete search history.

*Primary Examiner* — Susan McCormick Ewoldt

(57) ABSTRACT

A new cultivar of *Rosa* named 'ZARSBJOH' that is distinguishable by compact growth habit which requires limited pruning, dark green and glossy foliage and bright semi-double red well formed flowers. The flowers of 'ZARSBJOH' are semi-double and very long lasting, holding their color even in hot weather. 'ZARSBJOH' exhibits vigorous growth on its own roots, shows high disease resistance and is hardy to USDA Zone 5. In combination these traits set 'ZARSBJOH' apart from all other existing varieties of *Rosa* known to the inventor.

2 Drawing Sheets

Genus: *ROSA*.
Species: ×*hybrida*.
Denomination: 'ZARSBJOH'.

BACKGROUND OF THE INVENTION

This application is co-pending with the application for the inventor's variety of Shrub Rose Plant named 'ZARSBSUN'.

The present invention relates to a new and distinct cultivar of *ROSA* or shrub rose, grown as an ornamental plant for use in the garden and landscape. The new invention is known botanically as *ROSA×hybrida* and will be referred to hereinafter by the cultivar name 'ZARSBJOH'.

'ZARSBJOH' is a complex hybrid plant that is the product of a breeding program to create new and improved varieties of garden roses in all commercial classes.

'ZARSBJOH' was selected as a seedling that resulted from the controlled cross-pollination carried out by the inventor in a cultivated area of Somis, Calif., USA. The breeding began in 1985 by crossing an individual plant *Rosa×hybrida* (species, unpatented) as the female parent and an individual of *Rosa×hybrida* 'WEKsnacare' (unpatented) as the male parent. Seed was collected from hips formed on the female parent and coded as 20150, then sown with the intention of making a selection from the seedlings that resulted.

'ZARSBJOH' was selected in 2006 based on the criteria of disease resistance combined with bright red, well formed flowers, compact plant habit, good tolerance to cold, ease of propagation and vigorous growth on its own roots. Selection was conducted by the inventor, in Somis, Calif., USA. The unique traits that distinguish 'ZARSBJOH' from other varieties of *Rosa* known to the inventor are resistance to common rose diseases; rust, powdery mildew and black spot. Ease of propagation from softwood cuttings and vigorous growth on its own roots.

'ZARSBJOH' is distinguishable from the parents predominantly by flower and foliage amount and size.

The flowers of *Rosa* species (unpatented) female parent have very small red flowers, averaging 20 mm with a higher average petal count of 55 petals, whereas the flowers of 'ZARSBJOH' have an average flower size of 30-35 mm and the flowers have an average petal count of 25 petals.

The male parent 'WEKsnacare' (unpatented) has flowers with a smaller average petal count of 15 petals as well as a larger plant size of 60 cm×60 cm. whereas the flowers of 'ZARSBJOH' have a higher average petal count of 25 and a smaller plant size of 45 cm×30 cm.

'ZARSBJOH' exhibits a compact rounded habit, dark green glossy foliage, semi-double flowers that open as bright red, well formed flowers. The plants of 'ZARSBJOH' exhibit a long flowering period, typically May to early November. Cultural conditions include full sun, regular water and rich well-draining potting soil. 'ZARSBJOH' is hardy to USDA Zone 5 and grows to 60 cm in height and 45 cm in width at maturity.

The variety of *Rosa* which is considered by the inventor to most closely resemble 'ZARSBJOH' is *Rosa* 'JACrenim' (unpatented). 'JACrenim' is a shorter plant averaging 75 cm×50 cm in size, whereas 'ZARSBJOH' has an average plant size of 45 cm×30 cm.

The first asexual reproduction of 'ZARSBJOH' was conducted in 2006 in Somis, Calif., USA. The method of asexual propagation utilized was softwood cuttings. Since that time under careful observation, the distinguishing characteristics have been determined stable, uniform, and to be reproduced true to type in subsequent generations of asexual propagation.

SUMMARY OF THE INVENTION

The following traits have been repeatedly observed and represent the distinguishing characteristics of the new *Rosa* cultivar named 'ZARSBJOH'. These traits in combination distinguish 'ZARSBJOH' from all other existing varieties of *Rosa* known to the inventor. 'ZARSBJOH' has not been tested under all possible conditions and phenotypic differences may be observed with variations in environmental, climatic, and cultural conditions, however, without any variance in genotype.

1. 'ZARSBJOH' exhibits compact growth habit which requires limited pruning.

2. 'ZARSBJOH' exhibits dark green and glossy foliage.
3. 'ZARSBJOH' bears bright red well formed flowers whose diameter is 35 mm.
4. The flowers of 'ZARSBJOH' are semi-double and very long lasting, holding their color even in hot weather.
5. 'ZARSBJOH' exhibits vigorous growth on its own roots.
6. Plants of 'ZARSBJOH' exhibit a long flowering period, typically May to early November.
7. 'ZARSBJOH' reaches maturity after one year of growth: dimensions at maturity are 45 cm to 60 cm in height and 30 cm to 45 cm in width.
8. 'ZARSBJOH' shows high disease resistance.
9. 'ZARSBJOH' is hardy to USDA Zone 5.

BRIEF DESCRIPTION OF THE DRAWINGS

The accompanying color drawings labeled

The drawing labeled FIG. 1 depicts the entire plant in bloom.

The drawing labeled FIG. 2 depicts a close-up view of the flowers.

Figure 1:
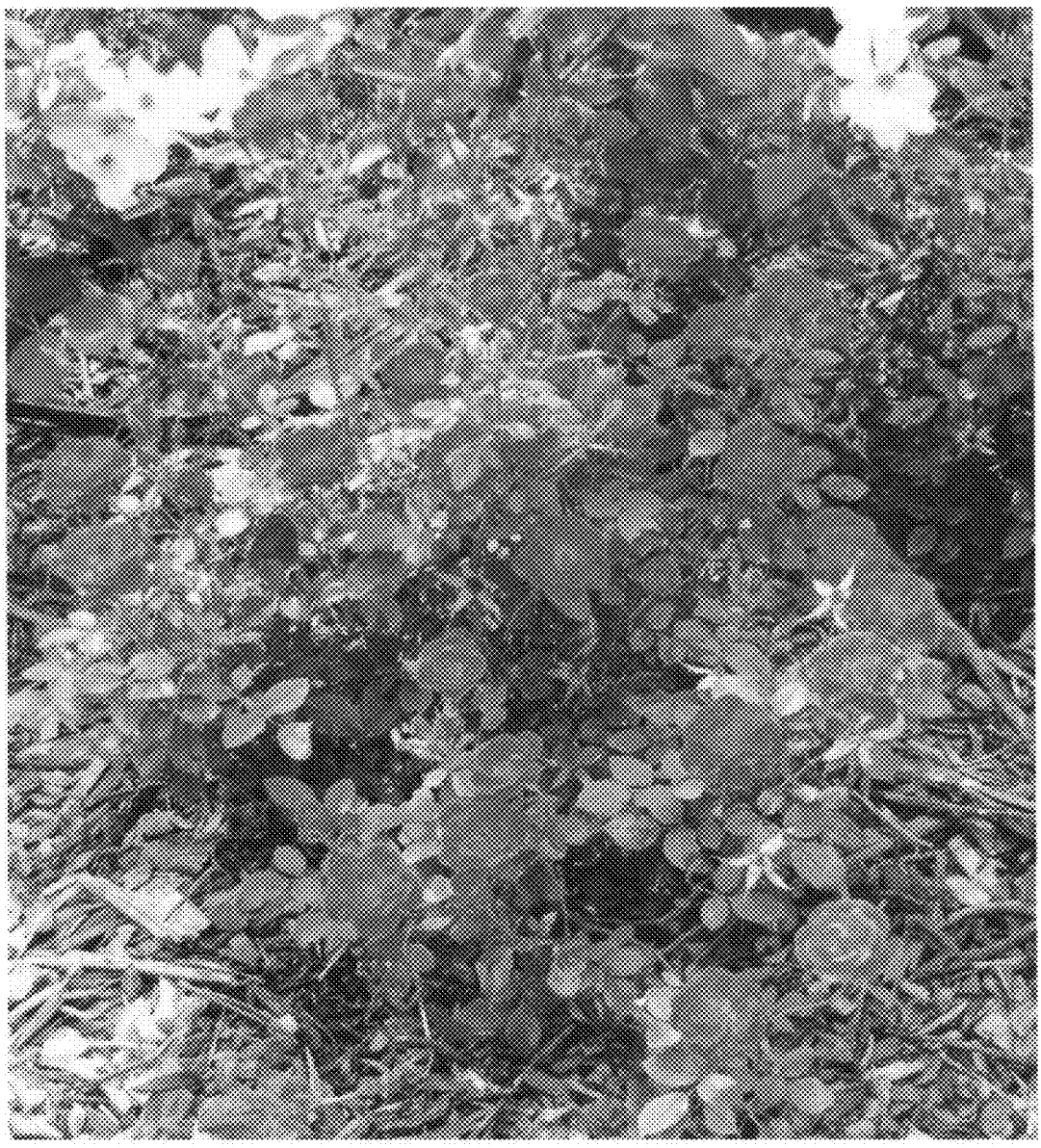
FIG. 1 and FIG. 2 illustrate the overall appearance of 'ZARSBJOH' showing the colors as true as is reasonably possible to obtain in colored reproductions of this type. Colors in the photographs may differ from the color values cited in the detailed botanical description, which accurately describes the actual colors of 'ZARSBJOH'.
Figure 2:
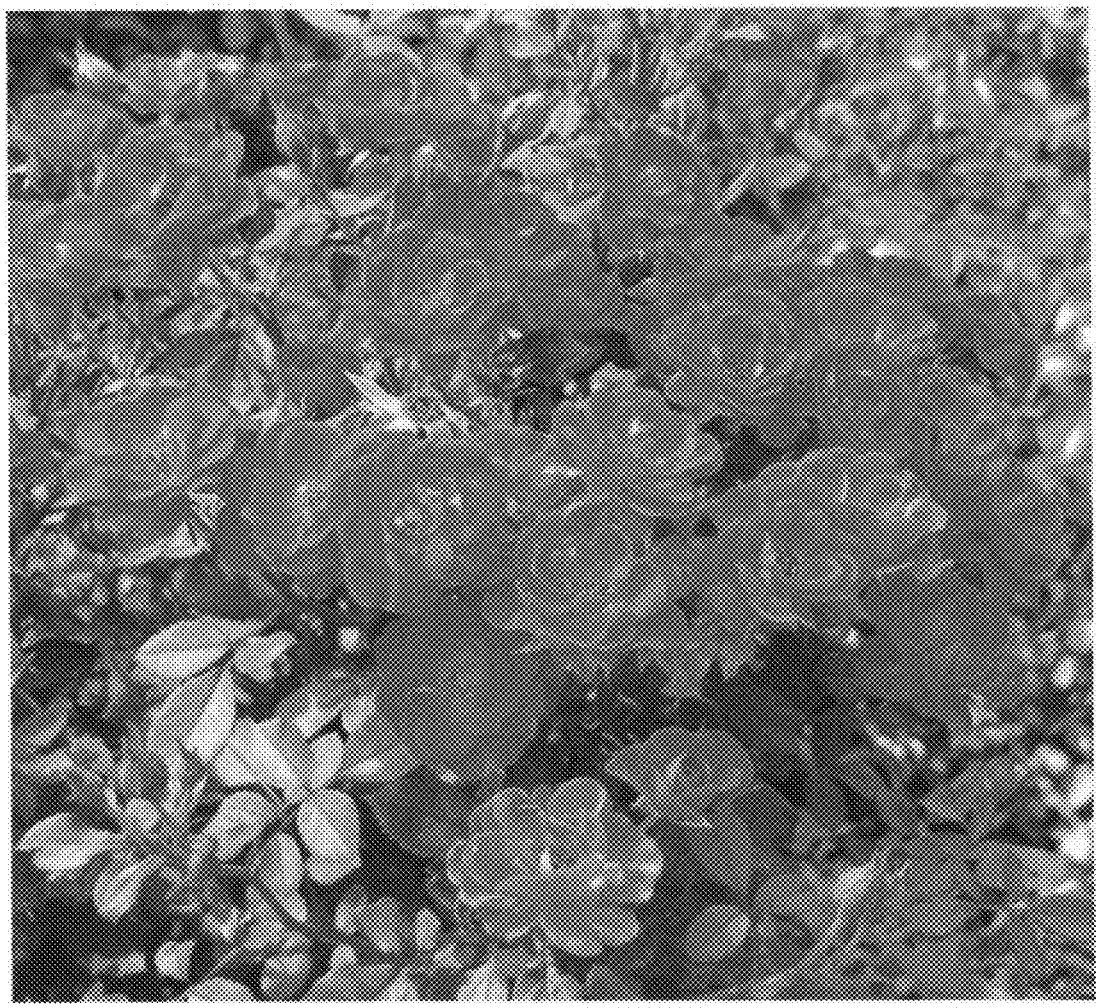

The drawings were made using conventional techniques and although flower and foliage color may appear different from actual color due to light reflectance, they are as accurate as possible by conventional photography.

BOTANICAL DESCRIPTION OF THE PLANT

The following is a detailed botanical description of the new *Rosa* cultivar named 'ZARSBJOH'. Observations, measurements, values and comparisons were collected in Troy, Ohio from a 12 month old plant grown in the landscape. Color determinations were made in accordance with The 2001 Royal Horticultural Society Colour Chart from London England, except where general color terms of ordinary dictionary significance are used. Growing requirements are similar to the species.

Botanical classification: *Rosa×hybrida* 'ZARSBJOH'.
Family: Compositae.
Genus: *ROSA.*
Species: *×hybrida.*
Denomination: 'ZARSBJOH'.
Common name: Rose.
Parentage: *Rosa×hybrida* 'ZARSBJOH' is a seedling that resulted from the controlled cross-pollination of the following parents.
- *Female parent.*—*Rosa×hybrida* 'WEKsnacare' (unpatented).
- *Male parent.*—*Rosa* Unnamed red miniature (unpatented).

Propagation method: Asexual soft-wood cuttings.
Rooting system: Fine and fibrous.
Vigor: Vigorous growth on own roots.
Habit: Upright compact habit.
Use: For use in the garden and landscape.
Type: Perennial.
Dimensions at maturity (one growing season): 45 cm to 60 cm in height and 30 cm to 45 cm in width.
Cultural requirements: Grow in full sun with regular water, and well-draining media.
Pest susceptibility: Susceptibility similar to the species.
Disease susceptibility: Resistant to common rose diseases: rust, powdery mildew and blackspot.
Hardiness: USDA Zone 5.
Stem:
- *Color, new wood.*—146D.
- *Color, old wood.*—146A.
- *Shape.*—Cylindrical.
- *Dimensions.*—Length: 30 cm-35 cm, diameter at base 1.5 cm, diameter below uppermost leaf 0.7 cm.
- *Bark surface.*—Smooth.
- *Internode length* (*range*).—10 cm-12 cm.

Prickles:
- *Quantity.*—Ordinary, on main canes from base: 1 every 2 cm of stem.
- *Quantity.*—Ordinary, on laterals from main canes: 1 every 2 cm of stem.
- *Form.*—Straight.
- *Length.*—5 mm.
- *Color, when young.*—180D.
- *Color, when mature.*—N200A.

Small prickles:
- *Quantity.*—On main stalk: None observed.
- *Quantity.*—On lateral stalks: None observed.

Foliage:
- *Type.*—Evergreen.
- *Leaf arrangement.*—Alternate.
- *Leaf division.*—Pinnate.
- *Leaf dimensions* (*average*).—8 cm in length and 5 cm in width.
- *Leaf color* (*adaxial surface*).—New foliage: 183A, mature foliage: 147A.
- *Leaf color* (*abaxial surface*).—New foliage: 183C, mature foliage: 147B.
- *Leaflets.*—Leaflet number (average): 5. Size: 60 mm in length×30 mm in width. Shape: Broadly oval. Base shape: Oblique. Apex shape: Acuminate. Texture: Leathery, glossy. Edge: Serrated. Serrations: Single. Petiole color: 146C. Petiole rachis, Color: 146C. Petiole rachis, Underside: Smooth with prickles. Auricles: Subulate. Stipules: Present, fused to petiole; length 10 mm, shape serrated. Disease resistance: Resistant to mildew, rust and blackspot under normal growing conditions. Pest resistance: None observed (insects). Resistant to common rose fungi. Vein color: 147B. Venation pattern: Reticulate.
- *Inflorescence.*—Inflorescence type: Terminal. Form: When first open: High and centered. Form: When mature: Flattens with age, outer petals curl back. Inflorescence quantity: Ranges between 20 and 30. Dimensions of inflorescence (average): 35 mm in diameter, 15 mm-20 mm in depth. Inflorescence shape: Radiate with center disk. Blooming seasons: Spring through fall.
- *Bud.*—Shape: Pointed ovoid, long. Dimensions (average): 16 mm in length and 11 mm in diameter. Color: When sepals first divide, bud color is 46A. Color: When half blown, the upper sides of the petals are 46A, lower sides are N34A. Sepals: Quantity: 5, shape spindly foliate with fine hairy and glandular margins. Of these, three are lightly appended and two are unappended. Sepals: Color: Upper surface: 138B. Sepals: Color: Lower surface: 146C. Sepal length: 16 mm. Sepal width: 5 mm. Sepal shape: Subulate. Receptacles: Color: 146B. Receptacle shape: Funnel.

Receptacle size: 5 mm in width and 6 mm in length. Receptacle surface: Smooth. Peduncle: Length short, averaging between 30 to 35 mm. Peduncle surface: Smooth with occasional very fine glands. Peduncle: Color: 146D. Peduncle strength: Stiff, erect and slender.

*Blooms*.—Size: Small, borne single, average open diameter 35 mm. Stems: Strength: Strong. Average length is 110 mm, with a diameter of 3 mm. Form: When first open: High and centered. Form: When mature: Bloom flattens with age, outer petals curl back. Petals: Number of petals under normal conditions: Average between 20 to 25. Petal color (upper surface): 46A. Petal color (lower surface): N34A. Petal color (base, both surfaces): Small 1 mm×1 mm color spot of 2C. Discoloration: Color does not change with age. Fragrance: None.

*Petals*.—Thickness: Thick, leathery. Surface texture: Smooth. Shape: Orbicular. Margin: Entire. Apex shape: Rounded. Base shape: Rounded. Form: Tips slightly recurved. Arrangement: Imbricated. Petaloids: None observed. Persistence: Petals drop off cleanly before drying. Lastingness: On the plant: Long, about 7 to 8 days. Lastingness: As a cut flower: Long, about 9 days.

*Reproductive organs*.—Stamens: Number: Average of 40 to 45. Length: 6 mm. Anthers: Length: 2 mm. Color: 164B. Arrangement: Regular around styles, mixed with occasional petaloids. Filaments: Color: 171B. Length: 4 mm. Pollen: Color: 164C. Pistils: Number: Average of 14 to 15. Length: 3 mm. Styles: Color: 180D. Length: 2 mm. Stigmas: Color: 160D. Length: 1 mm. Hips: Hips have not been observed during repeated observations.

The invention claimed is:

1. A new and distinct cultivar of *Rosa* plant named 'ZARSBJOH' as described and illustrated herein.

* * * * *